(12) United States Patent
Foos et al.

(10) Patent No.: US 12,318,233 B2
(45) Date of Patent: Jun. 3, 2025

(54) SYSTEM AND METHOD FOR AUTOMATED PROJECTION RADIOGRAPHY

(71) Applicant: CARESTREAM HEALTH, INC., Rochester, NY (US)

(72) Inventors: David H. Foos, Webster, NY (US); Eliot L Siegel, Severna Park, MD (US)

(73) Assignee: Carestream Health, Inc., Rochester, NY (US)

( * ) Notice: Subject to any disclaimer, the term of this patent is extended or adjusted under 35 U.S.C. 154(b) by 463 days.

(21) Appl. No.: 17/791,033

(22) PCT Filed: Nov. 18, 2020

(86) PCT No.: PCT/US2020/060938
§ 371 (c)(1),
(2) Date: Jul. 6, 2022

(87) PCT Pub. No.: WO2021/141678
PCT Pub. Date: Jul. 15, 2021

(65) Prior Publication Data
US 2023/0027305 A1    Jan. 26, 2023

Related U.S. Application Data

(60) Provisional application No. 62/957,831, filed on Jan. 7, 2020.

(51) Int. Cl.
*A61B 6/04* (2006.01)
*A61B 6/42* (2024.01)
*A61B 6/50* (2024.01)

(52) U.S. Cl.
CPC .......... *A61B 6/0492* (2013.01); *A61B 6/4208* (2013.01); *A61B 6/505* (2013.01)

(58) Field of Classification Search
CPC .... A61B 6/04; A61B 6/08; A61B 1/00; A61B 34/00; A61B 2034/107; A61B 6/469; A61B 6/467; A61B 6/468; A61B 6/547; A61B 6/46; A61B 6/54; A61B 6/545; A61B 6/40; A61B 6/4014; A61B 6/42
See application file for complete search history.

(56) References Cited

FOREIGN PATENT DOCUMENTS

| CN | 109 199 387 | 1/2019 | |
|---|---|---|---|
| CN | 110 353 711 | 10/2019 | |
| WO | WO-2020164713 A1 * | 8/2020 | ........... A61B 6/5258 |

OTHER PUBLICATIONS

International Search Report mailed on Apr. 28, 2021 for International Application No. PCT/US2020/060938, 2 pages.

* cited by examiner

*Primary Examiner* — Don K Wong

(57) ABSTRACT

Radiographic imaging identifies a subject anatomy for radiographic image content and automatically identifies a subject's position from one or more sensor signals. The imaging apparatus issues re-positioning guidance signals for re-positioning the patient. Signals are generated to set an imaging exposure technique and component positions according to data associated with the subject anatomy. A radiographic image of the subject is acquired according to the component and technique signals by automatically energizing the x-ray source. The acquired radiographic image is analyzed using trained logic to determine clinical diagnostic suitability of the image and to identify one or more abnormalities in the subject anatomy.

9 Claims, 6 Drawing Sheets

SYSTEM AND METHOD FOR AUTOMATED PROJECTION RADIOGRAPHY

CROSS REFERENCE TO RELATED APPLICATIONS

This application claims the benefit of and is a U.S. National Phase filing of PCT Application PCT/US2020/0060938 filed Nov. 18, 2020 entitled "SYSTEM AND METHOD FOR AUTOMATED PROJECTION RADIOGRAPHY", in the name of Foos et al., which claims benefit of U.S. Patent Application Ser. No. 62/957,831, filed Jan. 7, 2020, in the name of Foos et al., and entitled SYSTEM AND METHOD FOR AUTOMATED PROJECTION RADIOGRAPHY.

TECHNICAL FIELD

The disclosure relates generally to the field of radiographic imaging, and in particular to digital radiographic imaging systems that automate image acquisition, image processing, and diagnostic interpretation.

BACKGROUND

Flat panel digital radiography (DR) is a proven, safe, and effective modality for diagnosing patients who present various clinical indications such as suspected fractures, shortness of breath, injury following motor vehicle accidents or other trauma circumstances, and for patients in the critical care (intensive care unit) setting, such as to monitor respiratory status, for example.

The 2 dimensional (2-D) nature of DR however, can intrinsically constrain its diagnostic efficacy, particularly in more complex clinical situations. Conversely, three dimensional (3-D) computed tomography (CT) has become ubiquitous in radiology, and is emerging as the modality of choice for many types of more complex cases. CT is also now the standard of care for imaging patients who present indications wherein suspected abnormalities associated with the presented indications could be life threatening, e.g., lung cancer screening. The widespread adoption of CT is attributed to a combination of factors including superior clinical efficacy, reduced dose levels that are now possible with improved scanners, advanced volumetric reconstruction technologies, reduced equipment costs, and improved patient workflows. It is forecast that CT can eventually supplant DR as the standard of care for many types of diagnostic X-ray imaging.

Although CT imaging shows signs of growing proliferation and use in some areas, there remain applications wherein DR is a more suitable modality. In addition, given its inherent advantages such as proven performance, portability, and familiar workflows, as well as the leverage of technological advances such as artificial intelligence, DR imaging can be expected to continue to hold a valuable position as a viable diagnostic modality well into the future. In clinical environments, for example, higher cost and complexity of setup and operation can render CT a much less attractive an option than DR for routine diagnostic imaging examinations characterized by high patient throughput, particularly for repetitious exams used for high-volume screening and typically characterized by few inherent operational problems and relatively low occurrence of disease or condition requiring special handling. Annual health screening examinations, for example, routinely carried out for factory workers in some developing countries, can be very suitably served using DR with appropriate supporting tools.

Among practical approaches for improving the cost-effectiveness of DR is reduction of operational costs, or equivalently, minimizing the cost of ownership. Minimizing DR operational costs can be accomplished through process automation, which in turn, would enable reduction of radiographic technologist staffing levels and, further, reduce radiologist involvement in handling routine image interpretation.

In routine practice, radiographic imaging typically involves acquiring one or more standard views of patient anatomy. Positioning the patient for radiographic imaging is a manual task, executed or supervised by a trained technician or practitioner. Further, the patient is observed during exposure, such as to detect unintended movement or other problems that may compromise image quality and potentially require the radiographic examination to be repeated. Following acquisition of the radiographic image, the technologist or practitioner performs a quality control process step by visually reviewing the image for completeness, contrast, brightness, and sharpness, as well as other factors. If the acquired image is deemed acceptable, it is electronically disseminated (or printed) for diagnostic interpretation by a radiologist or a clinician. If the image is deemed unacceptable, the radiographic examination will be repeated. Some DR systems maintain and analyze quality control statistics which are subsequently used as a basis for improvement of quality assurance processes.

In light of the aforementioned, there is a need to improve the overall effectiveness of DR by reducing operational costs, making the overall DR imaging workflow more effective and efficient. In particular, automation of aspects of image acquisition and interpretation could help to reduce staffing resources required for radiography acquisition, can help to more systematically execute quality control and quality assurance processes, and may help to provide useful levels of radiographic interpretation for routine screening and other applications. At the same time the speed and consistency with which routine exams could be performed can be improved, thereby maximizing patient throughput.

Thus, it can be appreciated that there would be benefits to apparatus and methods that improve clinical imaging workflow and apply automated tools to the tasks of improving efficiency and quality for radiographic images.

SUMMARY

Objects of the present disclosure include advancing the art of radiographic image processing using DR systems and addressing areas of pressing need and correcting observed shortcomings noted previously in the background section. With these and related objects in mind, embodiments described herein address problems that hinder achieving improved efficiency of radiographic imaging workflow, particularly for DR imaging in clinical environments.

These objects are given only by way of illustrative example, and such objects may be exemplary of one or more embodiments of the invention. Other desirable objectives and advantages inherently achieved may occur or become apparent to those skilled in the art. The invention is defined by the appended claims.

According to one aspect of the disclosure, there is provided a method for radiographic imaging comprising identifying a subject anatomy for radiographic imaging based on data signals associated with the subject. A position of the subject relative to the imaging apparatus is automatically identified using one or more sensors that provide the data signals. Re-positioning guidance signals are provided by the imaging apparatus that communicate instructions to the subject so that the subject may reposition the subject anatomy. Signals for configuring and positioning at least an x-ray source and a DR detector are generated by the imaging apparatus. Technique signals are also generated to set imaging exposure based on the obtained data signals associated with the subject anatomy. The radiographic image of the subject anatomy is captured based on the one or more sensor signals and technique settings. Trained logic is used to analyze the captured radiographic image to determine clinical diagnostic suitability of the captured image. One or more abnormalities related to the subject anatomy may be identified using the trained logic to analyze the captured image. The assessment may be recorded and reported on a display coupled to the imaging apparatus.

According to another aspect of the disclosure, a radiography imaging system includes an x-ray source, a digital radiographic detector, fiducial markers positioned at electronically recorded locations, means for detecting a position of a patient anatomy relative to at least one of the fiducial markers, such as a camera, and means for outputting a visual and/or audio cue to the patient, such as a display or a speaker, to instruct the patient to move at least a portion of the patient's anatomy. A control system activates the source and detector to capture a radiographic image of the patient anatomy in response to detecting that the position of the patient anatomy relative to the at least one fiducial marker is acceptable.

BRIEF DESCRIPTION OF THE DRAWINGS

The foregoing and other objects, features, and advantages of the invention will be apparent from the following more particular description of the embodiments of the invention, as illustrated in the accompanying drawings. The elements of the drawings are not necessarily to scale relative to each other.

DETAILED DESCRIPTION OF THE EMBODIMENTS

Figure 1:
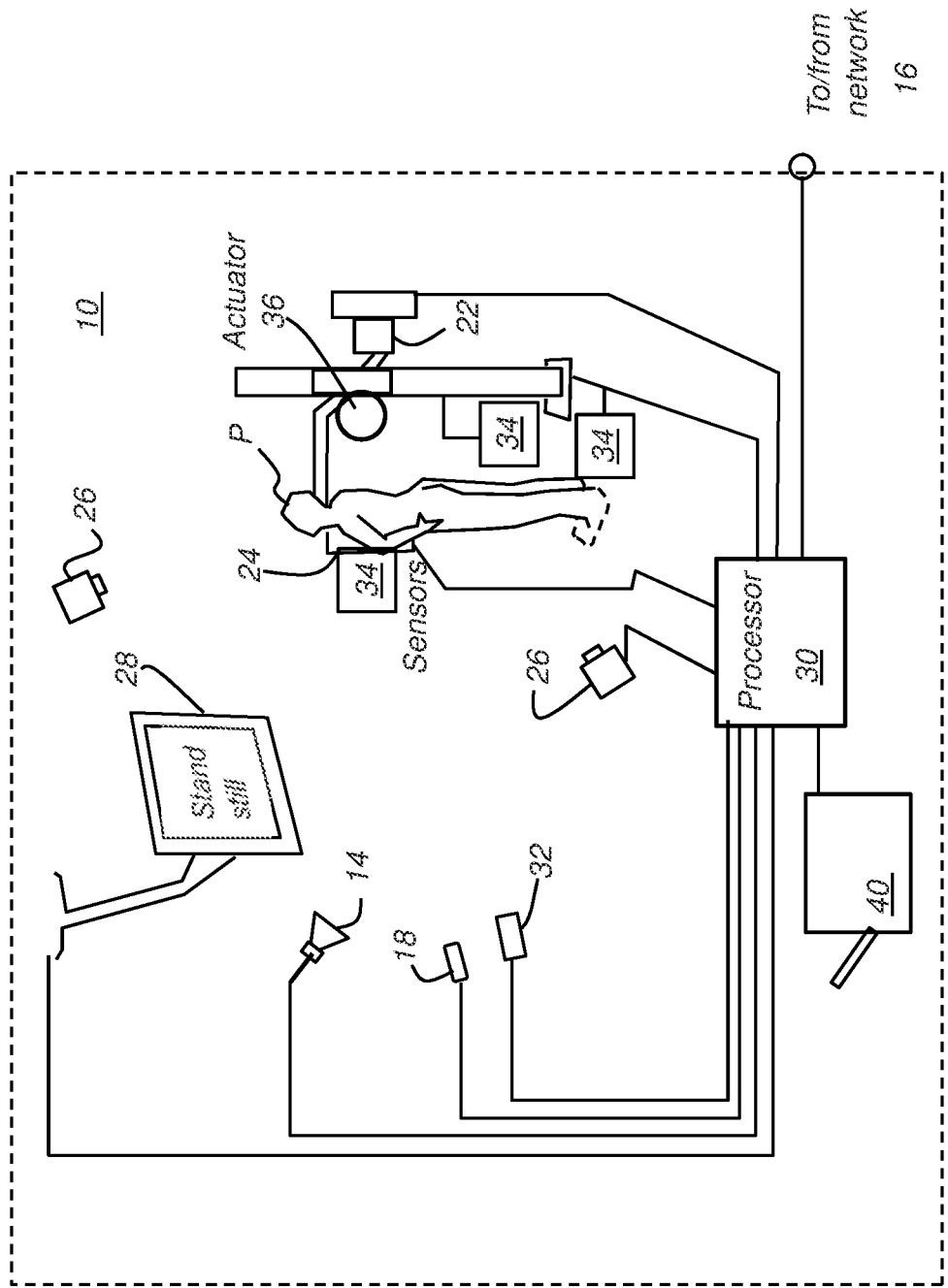
FIG. 1 is a schematic diagram of a standalone radiographic imaging system for automated operation.

This application claims the benefit of U.S. Provisional application U.S. Ser. No. 62/957,831, provisionally filed on Jan. 7, 2020, entitled "SYSTEM AND METHOD FOR AUTOMATED PROJECTION RADIOGRAPHY", in the names of Foos et al., hereby incorporated by reference herein in its entirety.

The following is a detailed description of the preferred embodiments, reference being made to the drawings in which the same reference numerals identify the same elements of structure in each of the several figures.

Where they are used, the terms "first", "second", and so on, do not necessarily denote any ordinal or priority relation, but may be used for more clearly distinguishing one element or time interval from another. The term "plurality" means at least two.

In the context of the present disclosure, the terms "viewer", "operator", and "user" are considered to be equivalent and refer to the viewing practitioner or other person who views and manipulates equipment, controlled by a processing system, for x-ray acquisition or an x-ray image itself on a display monitor. An "operator instruction" or "viewer instruction" is obtained from explicit commands entered by the viewer using an electronic input device, such as a computer mouse or keyboard entry.

The term "in signal communication" as used in the application means that two or more devices and/or components are capable of digitally communicating with each other via signals that travel over some type of signal path. Signal communication may be wired or wireless. The signals may be communication, power, data, or energy signals which may communicate data, power, and/or energy from a first device and/or component to a second device and/or component along a signal path between the first device and/or component and second device and/or component. Signal paths may include physical, electrical, magnetic, electromagnetic, optical, wired, and/or wireless connections between the first device and/or component and second device and/or component. Signal paths may also include additional devices and/or components between the first device and/or component and second device and/or component.

In the context of the present disclosure, the term "coupled" is intended to indicate an electrical, digital, or mechanical association, connection, relation, or linking, between two or more components. For mechanical coupling, two components need not be in direct contact, but can be linked through one or more intermediary components, such that the disposition of one component affects the spatial disposition of a component to which it is coupled.

As used herein, the term "energizable" relates to a device or set of components that perform an indicated function upon receiving power and, optionally, upon receiving an enabling signal.

The term "highlighting" for a displayed feature has its conventional meaning as is understood to those skilled in the information and image display arts. In general, highlighting uses some form of localized display enhancement to attract the attention of the viewer. Highlighting a portion of an image, such as an individual organ, bone, or structure, or a path from one chamber to the next, for example, can be achieved in any of a number of ways, including, but not limited to, annotating, displaying a nearby or overlaying symbol, outlining or tracing, display in a different color or at a markedly different intensity or gray scale value than other image or information content, blinking or animation of a portion of a display, or display at higher sharpness or contrast.

Embodiments of the present disclosure address the need to combine, into a single integrated system, the capability for highly automated radiographic imaging. In addition, alternate embodiments of the present disclosure provide solutions for automating each phase of the imaging process and for orchestrating how the various automated phases can work together in order to provide a flexible solution that automates particular phases of the process, while allowing various levels of interaction, coordination, and/or supervision to trained personnel assigned to administer or manage the imaging system.

In order to provide the level of automation needed for improved effectiveness and more widespread access to radiographic imaging, embodiments of the present disclosure can provide automation to support each of the following overall functions and capabilities:

(i) patient identification and verification;
(ii) identification of desired subject anatomy to be imaged;
(iii) capability for, and guidance to support, patient self-positioning for radiographic imaging;
(iv) automatic positioning of adjustable imaging system components, including receptor, x-ray source, and collimator appropriate to the positioned patient and to the subject anatomy to be imaged;
(v) automatic setting of exposure parameters;
(vi) automated management of the image acquisition process, including enabling the patient for actuating exposure and acquiring the radiographic image;
(vii) automated quality control and quality assurance processes executed by the system;
(viii) capability for automatic processing of the captured radiographic image for display;
(ix) automatic image interpretation and assessment;
(x) recording and reporting of diagnostic and clinically relevant assessment and findings related to the automated processing of the radiographic image content.

For execution and orchestration of the various tasks and capabilities listed hereinabove, embodiments of the present invention can employ trained logic, equivalently termed "machine learning" tools and capabilities. Trained or machine-learned logic can be distinguished from conventional programmed logic that is formulated by a programmer based on a formal instruction language that is used to specify particular data operations to be performed by a processor or processing system. In various embodiments, the processing logic circuits can include portions of executable code that have been generated using conventional procedural programming logic that provides a predictable response according to received inputs, as well as other portions of executable code that have been generated using machine learning techniques that are characterized as model-based and probabilistic, based on training using multiple examples, and provide solutions derived from heuristic processes. While aspects of the described solution are illustrated with respect to 2-D DR imaging, it should be understood that many of the same features and approaches can be similarly applied for advanced variations of DR imaging such as dual energy subtraction, digital tomosynthesis, and x-ray motion imaging, such as fluoroscopy.

The present disclosure describes a method and system intended to reduce operational costs and improve the diagnostic quality of routine radiology examinations when using DR.

In the preferred embodiment of the present disclosure, reduced radiology operational costs, reduced requirements for skilled staffing, improved diagnostic performance, lower cost of care for patients, and improved patient treatment and results can be realized.

An embodiment of the present disclosure, described following with particular reference to FIG. 1, can provide a fully automated system for obtaining orders for radiographic examinations of patients, positioning said patients for radiographie capture, capturing radiographie images of patients, processing the images of patients for distribution and display, and analyzing (and reporting) the findings obtained from said captured and processed patient images as described herein. An alternative embodiment of the present disclosure, described following with particular reference to FIGS. 2A and 2B, can provide a system for obtaining radiographic images having a centralized architecture that can reduce the workload of imaging staff and allow more active patient participation in the imaging workflow.

Figure 2A:
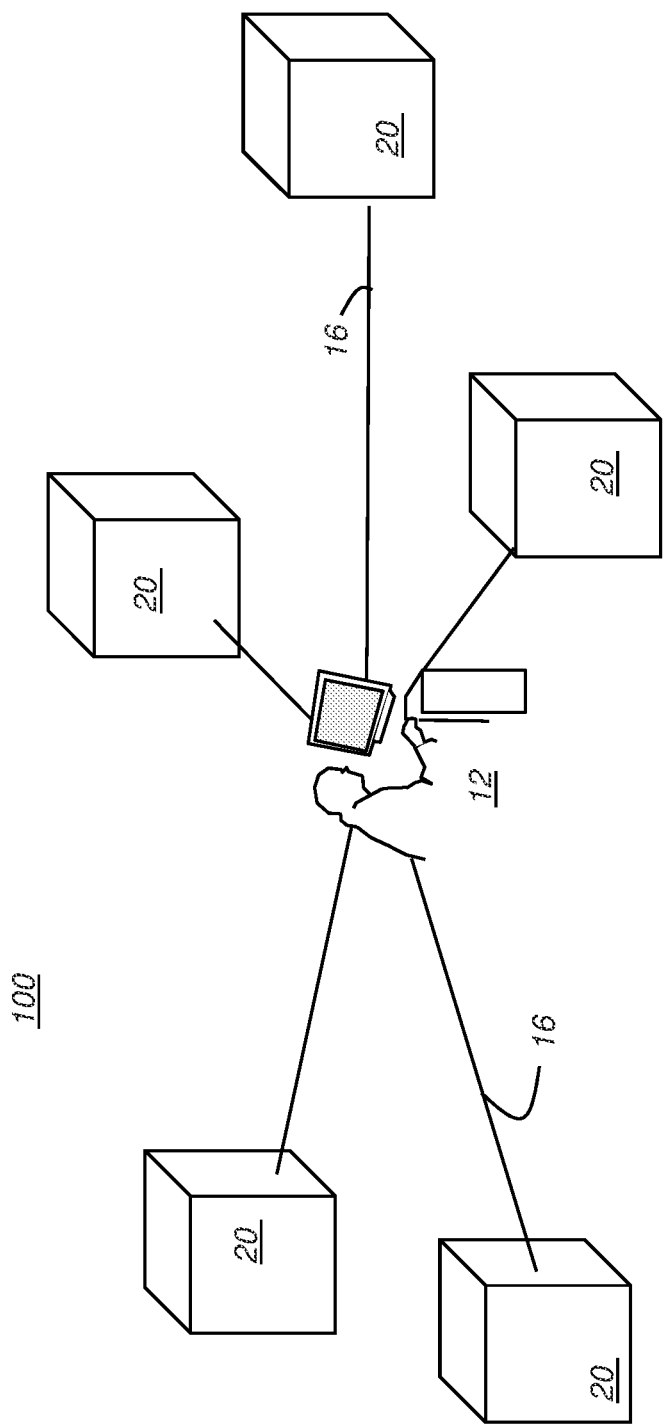
FIG. 2A is a schematic diagram that shows a radiographic imaging system having a central control console and one or more satellite imaging sites.
Figure 2B:
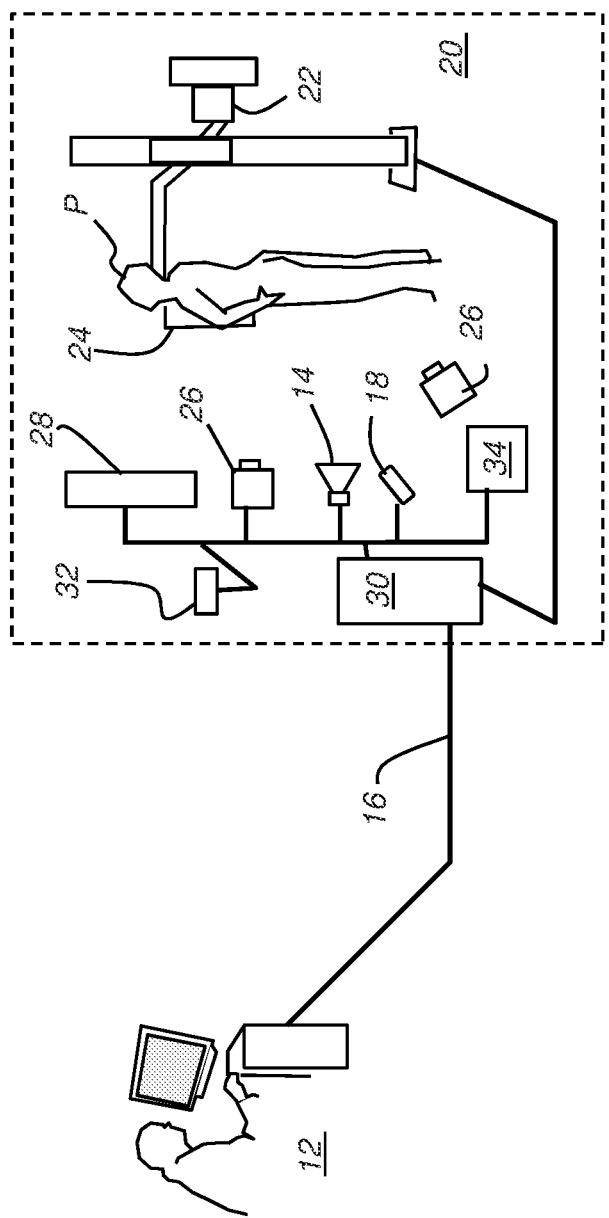
FIG. 2B is a schematic diagram that shows components of a satellite imaging site according to an embodiment of the present disclosure.
Figure 3:
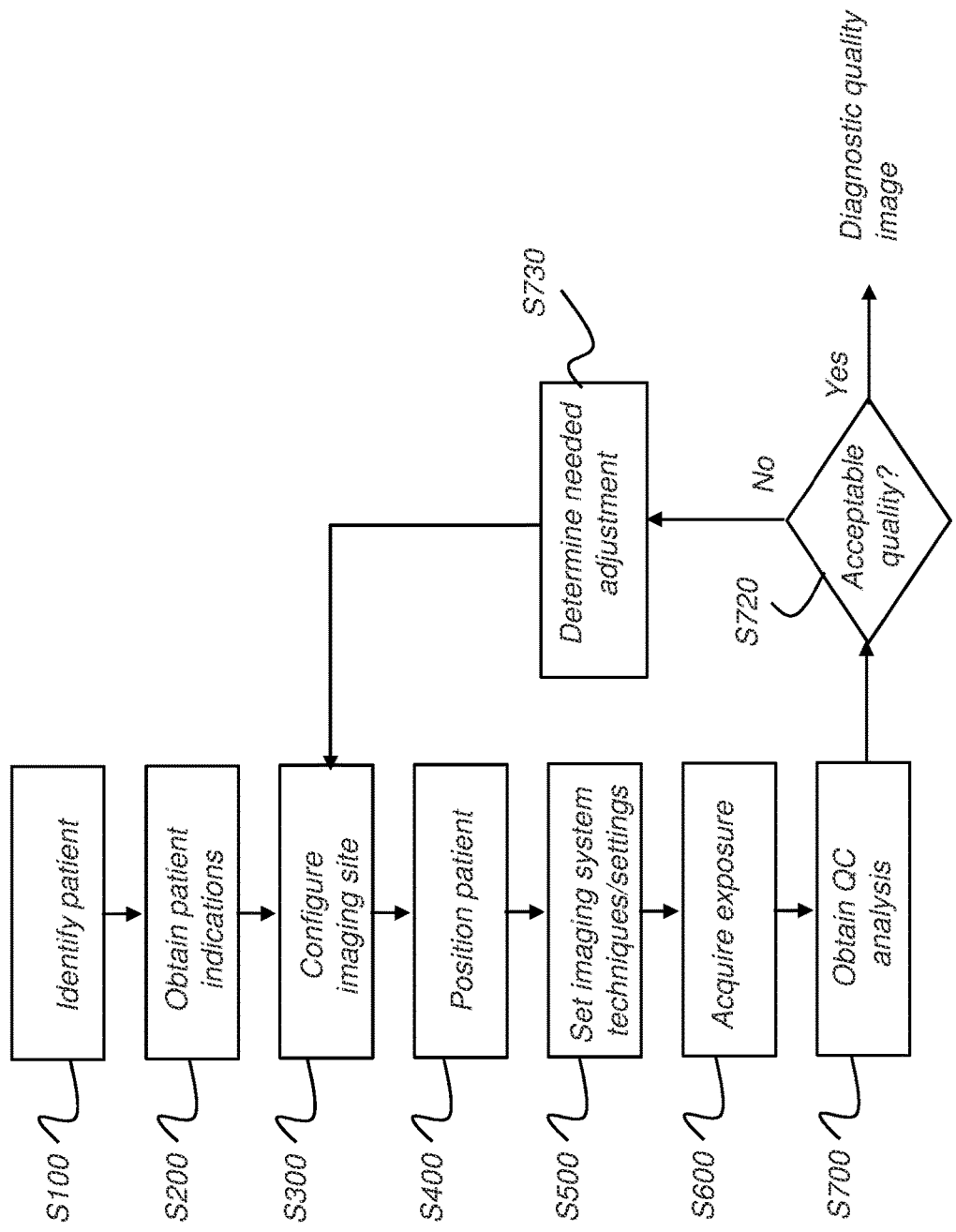
FIG. 3 is a logic flow diagram showing an exemplary workflow for imaging acquisition using a satellite site arrangement.
Figure 4:
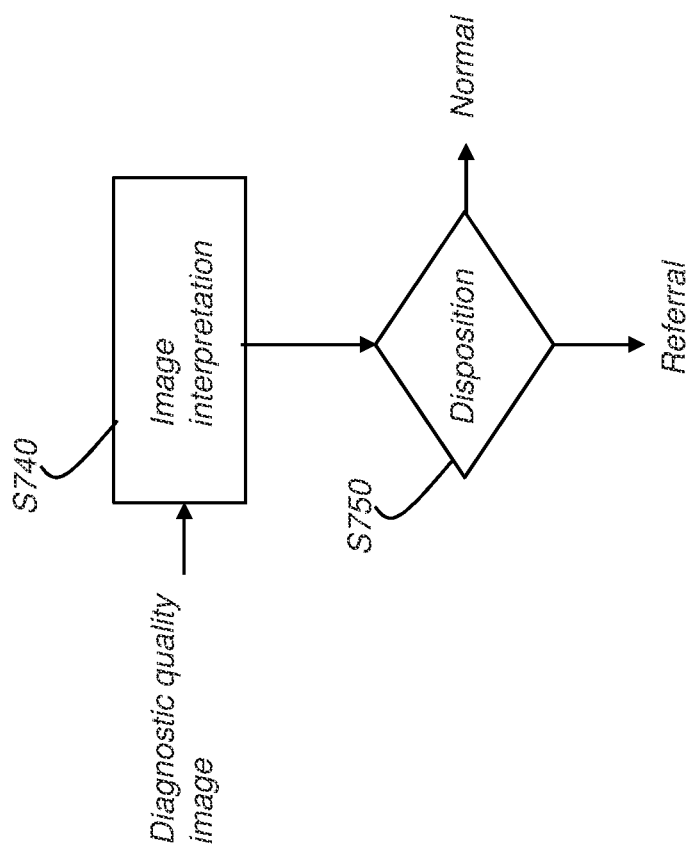
FIG. 4 is a logic flow diagram that shows a follow-up sequence for automated processing and disposition of an image acquired using the sequence of FIG. 3.

FIGS. 3 and 4 show various processing steps that can be used in the imaging sequence with the systems shown in any of FIG. 1, 2A or 2B; individual steps are described in more detail subsequently.

Embodiment Providing Standalone Radiographic Imaging

By way of example, the schematic diagram of FIG. 1 shows a radiographic imaging system 10 that provides patient imaging in a stand-alone configuration for unassisted operation. The system architecture of FIG. 1 can be appropriate, for example, as a portable apparatus transported to remote sites on a van or other vehicle, or available for as-needed access at a local facility. This system could alternately be installed, for example, in an office or facility wherein no assistance is typically needed for the type of exams to be performed and the likelihood of finding serious patient conditions is small or urgency of response is not typically provided. As just one example, procedure for standard chest x-rays for ambulatory patients in a clinical environment most often follows a conventional procedure and does not generally require special techniques or assistance for patient preparation and positioning. Periodic chest exams for employees at a company site may be standardized and, other than being used under some supervision, may not require individualized setup and execution by highly trained radiographic staff.

A useful aspect of the FIG. 1 arrangement is that resources for radiographic acquisition can be distributed to geographical areas wherein demand for imaging may vary from one period to the next or wherein regular access to clinical services can be difficult to provide, such as in remote rural areas or in disaster-affected areas, for example. Exam information and results can be maintained by the patients themselves or may be transferred to a central site or other networked site for assessment or for assignment to particular practitioners or facilities, as well as for storage.

Although the stand-alone system of FIG. 1 could enable self-setup and acquisition by patients themselves, an alternative arrangement would enable an acquisition environment wherein the patient requires only a minimum of on-site assistance and oversight for standard exams, without the need or availability of centralized control.

In one alternative embodiment, the system of FIG. 1 can be used independently, providing a self-contained and highly automated imaging station for "self-serve" radiographic imaging. Some form of access control to the site facility and to site functions can be provided, such as by authorization from a practitioner via an exam order or other permission. Standard protections, password protection, and other techniques can be used to secure the equipment from possible tampering and misuse.

The schematic diagram of FIG. 1 shows an exemplary arrangement for components of a standalone imaging system 10 for imaging a patient P according to an embodiment of the present disclosure. Imaging system 10 has an x-ray source 22 and DR detector 24, which may be mounted on a bucky or other standard mounting or positioning device. A processor 30 controls the local x-ray generator and system and communicates commands and data with the DR detector 24, such as through a wired or wireless connection. One or more movable, network connected cameras 26 and/or other types of sensors 34 can be selectively coupled to a remote display to allow monitoring of the site by remote staff, including identification of patient P position, identification of acquisition component position, and presence of onsite staff and other authorized or unauthorized persons, for example. Camera 26 can be a 3D depth camera for more accurately detecting body part position.

A display 28 can allow visual communication with the patient and staff at a remote site, such as for verifying patient P identification, for rendering instructions to the patient on posture, position, and behavior, and for indicating when patient motion is or is not allowable, for example. A light projector 32 can be used to project guidance markers or other types of fiducials, also termed fiducial markers, to aid in patient positioning. Fiducial placement can be dependent, at least in part, on the anatomy to be imaged. An optional speaker 14 and microphone 18 can allow audio communication between the patient P and radiography assistance personnel.

Staffing for use of system 10 may not require a highly trained technician in some environments. Thus, for example, a technician with more general health and safety skills can be employed to maintain system 10, validating system operation and performing any needed tasks for periodic testing, assisting the patient to follow positioning instructions and to conform with exposure precautionary requirements, and other guidelines A number of sensors 34 can also be provided, along with additional cameras or other devices, for detecting the proper positioning of anatomy and various conditions, such as the presence of other people at the satellite site and within the exposure area.

A printer 40 or other suitable output device can be provided in order to give the patient sufficient information and results related to the particular radiographic exam. The patient can also retrieve a printed or electronic copy of imaging results. A network connection 16 can allow information transfer as well as image transfer to and from the system site from and to other remote locations. It must be emphasized that while embodiments of the present disclosure can be used to support the configuration and operation of the standalone imaging apparatus, there can be a number of imaging conditions wherein unassisted or unsupervised operation is not an acceptable option. Proper acquisition, setup, imaging, and analysis of image data may require a higher level of supervision, but without conforming to rigorous requirements for routine radiographic imaging.

Processor 30 can be configured to execute both conventional, programmed software and machine learning or trained logic to execute each of the functions and capabilities (i)-(x) listed above, as described in more detail subsequently. Software organization can be in modular form, with the sequence of execution orchestrated by processor 30.

Embodiment Using Centralized Hub-and-Spoke System Architecture

An alternative embodiment can provide automated radiographic imaging with the advantage of some level of oversight and management, such as from a central site, for example. Referring to the schematic diagram of FIG. 2A, there is shown an embodiment of a radiographic imaging system 100 having a hub-and-spoke network architecture, with a central control console 12 and one or more satellite imaging sites 20 that can be monitored and controlled over a network from control console 12. A wired or wireless network 16, such as the Internet or other signal communication medium or mechanism can be used to provide a communications channel for transfer of instructions, images, and other data content, including audio and video data for example, between sites 20 and the control console 12. The various satellite sites 20 can be at any distance from control console 12, such as in the same room, the same or an adjacent building, or several minutes or hours away. Control console 12 can provide a second, remote display that shows image content from site 20.

The system architecture shown in FIG. 2A presents a novel paradigm for radiographic image acquisition, some or all parts of which may be adaptable and useful, particularly where standard types of imaging are needed and special techniques, highly trained personnel, or complex support equipment are not needed. The system architecture of FIG. 2A can be appropriate, for example, in an office or facility where only minimal patient assistance is typically needed for the bulk of the patient population. As just one example, the workflow process for standard chest x-rays for ambulatory patients in a clinical environment most often follows a conventional procedure and does not typically require special techniques or assistance for patient preparation and positioning. Periodic chest exams for employees at a site may be standardized and not require individualized setup and execution by highly trained radiographic staff. At the same time, some level of staff monitoring may be advisable, such as to help prevent error and reduce the number of retakes, for example.

Another useful aspect of the FIG. 2A arrangement is that resources for radiographie acquisition can be allocated among multiple areas wherein demand for imaging may vary from one period to the next or wherein regular access to clinical services can be difficult to provide, such as in remote rural areas or in disaster areas, for example. Multiple exams, each at a different site, can execute simultaneously, providing image data to a central site for assessment or for assignment to particular practitioners or facilities.

Although the satellite system of FIG. 2A could enable self-setup and acquisition by patients themselves, an alternative arrangement would enable an acquisition environment wherein the patient requires only a minimum of on-site assistance and oversight for standard exams, with centralized control applied for more complex decision-making such as default technique setting and for acquisition and processing of the obtained image content.

Yet another alternative embodiment of the present disclosure is highly automated, wherein central control console 12 employs machine learning to oversee the functioning of a network of imaging sites 20, each imaging site 20 having automated systems that allow patients, with minimal or no site support, to operate the imaging equipment, including image setup, acquisition, and disposition. For such a distributed system, central control console 12 can then serve as a collection point for storing and managing acquired images, for data acquisition and analysis, and for billing and administrative management functions. The schematic diagram of FIG. 2B shows an exemplary arrangement for components of satellite imaging site 20 for imaging patient P with at least a minimum of assistance according to an embodiment of the present disclosure. Similar to system 10 of FIG. 1, imaging site 20 has an x-ray source 22 and DR detector 24, which may be mounted on a bucky or other standard adjustable or movable mounting or positioning device. Processor 30 controls the local x-ray generator and system and communicates commands and data with the DR detector 24, such as through a wired or wireless connection. One or more cameras 26 and sensors 34 can allow monitoring of the site, including patient P position, acquisition component position, and presence of onsite staff and other authorized or unauthorized persons, for example. Display 28 can allow visual communication with the patient and staff, such as for verifying patient P identification, for instructing the patient on posture and position, and for indicating when motion is or is not allowable, for example. Light projector 32 can be used to project guidance markers to aid the patient or remote viewer in patient positioning. Speaker 14 and microphone 18 can allow audio communication between the patient P and control console 12 personnel.

Staffing of satellite site 20 may not require a highly trained technician in some environments. Thus, for example, a technician with more general health and safety skills can be employed at satellite site 20, assisting the patient to follow positioning instructions and to conform with exposure precautionary requirements, and other guidelines A number of sensors 34 can also be provided, energized to generate signal output in response to detected conditions, along with additional cameras or other devices, for detecting the proper positioning of anatomy and various conditions, such as the presence of other people at the satellite site and within the exposure area.

It must be emphasized that while embodiments of the present disclosure can be used to support the configuration and operation of the hub-and-spoke radiographic imaging system 100 as described, not all of the capabilities of the FIG. 2A and FIG. 2B systems might be implemented or necessary for a particular distributed system. One or more aspects of the present disclosure can help to improve workflow and efficiency of smaller scale, independent imaging sites, even without the centralized control described with reference to FIGS. 2A and 2B.

As FIGS. 1, 2A, and 2B have shown, there can be a number of alternative configurations for radiographic imaging using varying amounts of automation in order to support patient imaging.

The flow diagram of FIG. 3 describes a sequence of operation that can be applied, wholly or in part, to improve the delivery and accuracy of radiographic imaging services for generating diagnostic quality images in a range of different environments. Various tasks within this sequence can be particularly advantaged where implemented using logic tools trained by machine learning, as described in more detail subsequently.

Identifying Patient and Images Needed

Referring to FIG. 3, in a patient identification step S100, the patient identity is electronically received and verified by the system. Verification of patient identity can use any of a number of standard mechanisms, such as an electronic identification card or device, or may simply involve manual entry on a terminal at the satellite site, fingerprint detection, or other standard method. Upon arrival at the imaging site, the patient can log into the system using suitable identification numbers, e.g., patient name and date of birth, employee number, or other identification number.

For executing processes related to patient identification and verification, processor 30 can use conventional programmed logic or trained logic based on machine learning, or some combination of these alternative logic methods. By way of example, the patient P may scan an identification card, use a touch device for fingerprint identification, or enter data at a terminal associated with system 10 to establish identity. Alternately, camera 26 may be used to obtain an image of the patient and provide this information to processor 30 for matching with a stored patient image verified by an operator or by a facial recognition function executed by the system. Microphone 18 can alternately be used to record patient P speech and match the recorded speech pattern to the patient's stored speech records accessible to processor 30.

In an obtain patient indications step S200, for identifying desired subject anatomy to be imaged, some type of data signals associated with the patient are acquired. For example, the patient may provide information by data entry at an associated terminal or by verbal description acquired and interpreted by processor 30. Alternately, this information associated with the patient may be provided over network 16 connection, following identification of the patient. According to an embodiment of the present disclosure, an exam order can be issued from a referring physician. The exam order can be obtained through electronic means or can be entered as data signals into the system by manual means such as by scanning a code from a paper document, logging into an assigned site or account, or automatic tracking of required exams using the patient ID, for example. The exam order can include patient demographic information as well as information that prescribes the specifics of the radiographic image(s) to be captured such as the body part(s), projection(s), as well as left or right side(s).

According to an embodiment, the exam order can be on demand from the patient, practitioner, or qualified caregiver, such as in the case of a suspected sprain, broken bone, or similar localized condition.

Initial Configuration of Imaging System

After tasks of obtaining patient identification and indications, with the subject anatomy identified, steps that follow in the FIG. 3 sequence then prepare both the patient and the imaging system for exposure and image acquisition. A configuration step S300 performs an initial configuration of the imaging system at the satellite site. Depending on the exam involved, configuration step S300 can have a number of aspects and may require some activity at the satellite site. For example, the imaging components can be at least coarsely positioned for imaging the appropriate patient anatomy. More precise positioning can depend on factors such as patient height and overall size, constraints on patient movement (for example, patient unable to stand or bend), and standard equipment configuration used for the particular image type.

Using either the standalone system of FIG. 1 or the hub-and-spoke embodiment described previously with respect to FIGS. 2A and 2B, positioning of radiography components of system 10 or at satellite site 20 can be automated, effected by configuration signals that are generated by processor 30. Executing either programmed or trained logic, processor 30 can control a detector actuator 36 (FIG. 1) and source actuator 36 for translating the DR detector 24 and x-ray source 22 to achieve at least coarse positioning with respect to the target anatomy and, optionally, for more precise positioning needed for image acquisition. Alternately, with the FIG. 2A, 2B embodiment, using a set of motors or other actuators that control component movement and orientation, positioning can be performed in response to one or more commands issued to the site from the central control console 12.

According to an alternate embodiment of the present disclosure, actuators 36 may not be provided for DR detector and x-ray source 22 movement. Instead, the patient may be instructed by the system to manually adjust the position of the DR detector 24 and/or the position of the x-ray source 22, such as following information presented on display 28 or in response to audible tones or instructions. The positioning guidance can alternately be presented in the form of animations rendered to the display, for example, taking into account the size and condition of the patient P, as determined according to images from camera 26. Feedback signals from sensors 34 or camera image content can be used to ascertain the present position of imaging components. A range of allowable positions can be provided, with appropriate threshold settings for spatial positioning, such as for source-to-image distance (SID). The logic for re-positioning guidance signals can be provided from programmed instructions or can be trained logic generated using machine learning. Repositioning guidance signals that are issued can be audible tones, voice, or other auditory signals. The re-positioning guidance signals can alternately be used to energize one or more indicators.

As a further part of configuration step S300 in FIG. 3, an embodiment of the present disclosure includes one or more visible fiducial markers pre-positioned on or near detector 24 in order to guide patient P positioning by instructing the patient to position selected patient anatomy relative to the fiducial markers. For each type of image that is obtained, or for each type of anatomy to be imaged, a corresponding, predetermined arrangement of fiducial markers may be used. Fiducial markers can be disposed at positions visible to the patient or remote viewer, and can be electronically recorded in a system memory such that the precise positions of the fiducial markers are known relative to a DR detector's imaging area, for example. Processing of acquired radiographic images may include superimposing fiducial marker positions on the acquired radiographic images. In one embodiment, the positions of the fiducial markers may be superimposed, together with a virtual DR detector imaging area, on a display showing a position of the patient anatomy relative thereto during patient positioning and imaging. As described herein, the fiducial markers may be projected by a light projector 32, and may comprise a variety of shapes, such as an illuminated spot projected by laser light source.

For step S300, the patient, or assisting staff at the satellite site where available, can receive audible or visual instructions to assist in setup functions. Cameras 26 (FIG. 2B) or sensors 34 can be used to provide feedback information related to equipment setup, such as height, lateral positioning, angular orientation, source-to-imager distance (SID) or other spatial disposition for source, detector, and other components. When the system setup is suitable for the subsequent step of positioning the patient and performing any final adjustments, the system can then communicate, such as by audible or visual cue, when it is ready for the patient to be in position for imaging.

Continuing with the FIG. 3 sequence, a patient positioning step S400 then executes, in which the patient P follows verbal or visual instructions for anatomy positioning against DR detector 24, optionally as guided by the one or more visible fiducial markers formed, projected, or placed on detector 24 in order to assist the patient in positioning his or her anatomy relative to the fiducial markers.

Positioning cues that are provided to the patient by the system can be based on a number of factors, including:
  (i) specifics of the exam order, specifying type of exam, body part, projection, and side;
  (ii) information from the one or more cameras obtaining images that show the patient and patient positioning; and,
  (iii) electronic assessment of the position of the patient body part and projection to be imaged relative to any fiducial markers.

Fiducial markers can help to guide the positioning of the patient, including the disposition of various anatomy such as limbs, joints, chest, and head position, for example.

The fiducial markers themselves can be boundary lines, targets, and other references or shapes generated using projected patterns of light directed from the collimator.

Alternately, the fiducial markers can be physical markers, formed of any suitable material, and attached to the DR detector or its cover or to other structures in the imaging area. The fiducial markers can be radio-opaque, such as conventional lead markers familiar to those skilled in radiography, or can simply be markings that guide patient positioning against the DR detector.

The processor 30 logic for patient positioning can employ programmed or trained logic.

Continuing with the FIG. 3 sequence, with the patient properly positioned relative to the fiducial markers, the final configuration of the imaging geometry and exposure technique can be performed in a final configuration step S500. This process can involve final adjustment of X-ray source position, source-to-image distance (SID) and source orientation. In addition, collimator blade settings can also be adjusted.

It can be appreciated that all or some of the equipment settings can be automatically controlled, such as from the central control console. However, it may be more practical to have the setup of the x-ray components performed by staff at the satellite site. Technique settings such as mAs and kVp exposure parameters can be automatically set to appropriate values that take into account patient build or anatomy thickness, for example.

The processor 30 logic for generating one or more technique signals that set exposure technique parameters can employ programmed or trained logic.

Exposure Control

By interpreting sensor 34 signals and, alternately, image content from camera 26, the system can detect when the patient is properly positioned, and all hardware and software parameters are set and ready for the X-ray exposure. As shown in FIG. 3, an acquisition step S600 can then execute. Preparatory to acquisition, the system can indicate to the patient that the exam is ready to be performed. This indication can be audible or visual and may further include illumination of a warning light or other cautionary device to alert staff at the site and anyone in the proximity of the x-ray generator. The system may further indicate to the patient to remain still, or provide other information that may be helpful to the patient to minimize the likelihood of an improper exposure and/or need for a repeat exam. Acquisition can then be initiated from the central console, initiated by the local staff, or simply actuated within a given time period. An audible countdown can be provided for indicating time to exposure.

To allow for some variation in apparatus and patient positioning, the system processor 30 can check measured spatial values against various threshold parameters or acceptable sensor signal levels in order to determine imaging readiness and suitability. Thus, for example, some suitable tolerances can be allowed for SID or other dimensional values; provided the positional coordinates are within tolerance, imaging can proceed.

According to an alternate embodiment of the present disclosure, exposure can be initiated by the patient. Self-initiation can be provided along with system checks that act as interlocks. For example, it may be possible to enable the patient to perform prep and exposure when at least the following conditions can be detected:

(i) patient and exam have been correctly identified;
(ii) exposure space is secured and there are no other persons within a designated exposure area;
(iii) proper positioning of patient, DR detector, and x-ray source; and
(iv) setup of appropriate x-ray technique settings.

Trained logic can be used to respond appropriately to all of the necessary pre-conditions for exposure, as well as automated management of the image acquisition process, including enablement of the patient for actuating and acquiring the radiographic exposure. The trained logic can also determine the exposure period, for example.

Applying any level of supervision and assistance, using the system as described herein can increase patient participation in the imaging workflow. As just described, the steps provided in the FIG. 3 sequence can even enable patients to capture their own radiographic images, where this would be permitted, without the direct assistance of a qualified radiographic technologist. In another embodiment of the present invention however, a technologist or radiographer allows the system to automatically setup the patient and imaging hardware and software settings for exposure, leaving final verification checks and exposure actuation to be performed by the technologist, either at the satellite site or from the central control console.

Initial Image Analysis

Following image acquisition, the image can be automatically analyzed by software algorithms for quality control purposes in a QC analysis step S700, in order to determine whether or not the image is suitable for clinical diagnostic use. To assess clinical diagnostic suitability, images can be analyzed for overall quality problems such as excessive noise, anatomy cutoff or image clipping, unacceptable rotation with respect to the intended projection, presence of foreign objects such as jewelry that could impede interpretation, motion blur, sufficient contrast, capture of the proper side (left or right), absence of reference marks or incorrect markers or fiducials, and proper exposure level, e.g., exposure index. This analysis can use conventional image processing algorithms that have been developed to identify imaging problems or can alternately use machine learning or trained logic software that has been trained to identify suitable images from a set of obtained images.

Once the automatic quality control analysis is complete, a test step S720 determines whether or not the image has clinical diagnostic suitability, acceptable as a diagnostic quality image from both an image quality standpoint and from the perspective of the exam(s) that were ordered. The system can report results to the patient and to any attending staff and may indicate that the exam is complete and release the patient from the imaging center. Where the image does not appear to meet quality standards, an adjustment determination step S730 determines any needed adjustments and directs appropriate signals to configuration step S300 or, alternately, to final configuration step S500 for making any needed changes to allow the exam to be re-taken.

A text report can be provided to document image suitability, such as to certify acceptable image quality or to indicate conformance to quality control requirements for clinical diagnostic use, for example.

Image Interpretation

The optional sequence shown in FIG. 4 continues automated processing of the radiographic image resulting from the FIG. 3 sequence. According to an embodiment of the present disclosure, the image can be routed to a central radiographic image interpretation facility for executing an optional image interpretation step S740. The image content can be interpreted using artificial intelligence-based decision support algorithms, also termed machine learning module(s), that have been trained to detect abnormalities of various types and to provide annotation for the acquired images and to report on possible patient conditions. According to an alternate embodiment, processor 30 can execute trained logic that performs and reports on radiographic image interpretation. The processor can record and report results of image interpretation and assessment, such as on a display or control console, for example both at the patient's site and at a remote site.

In a disposition step S750, the system can disseminate images and computer-generated results to appropriate recipients for further interpretation and analysis.

Patient Positioning

Figure 5:
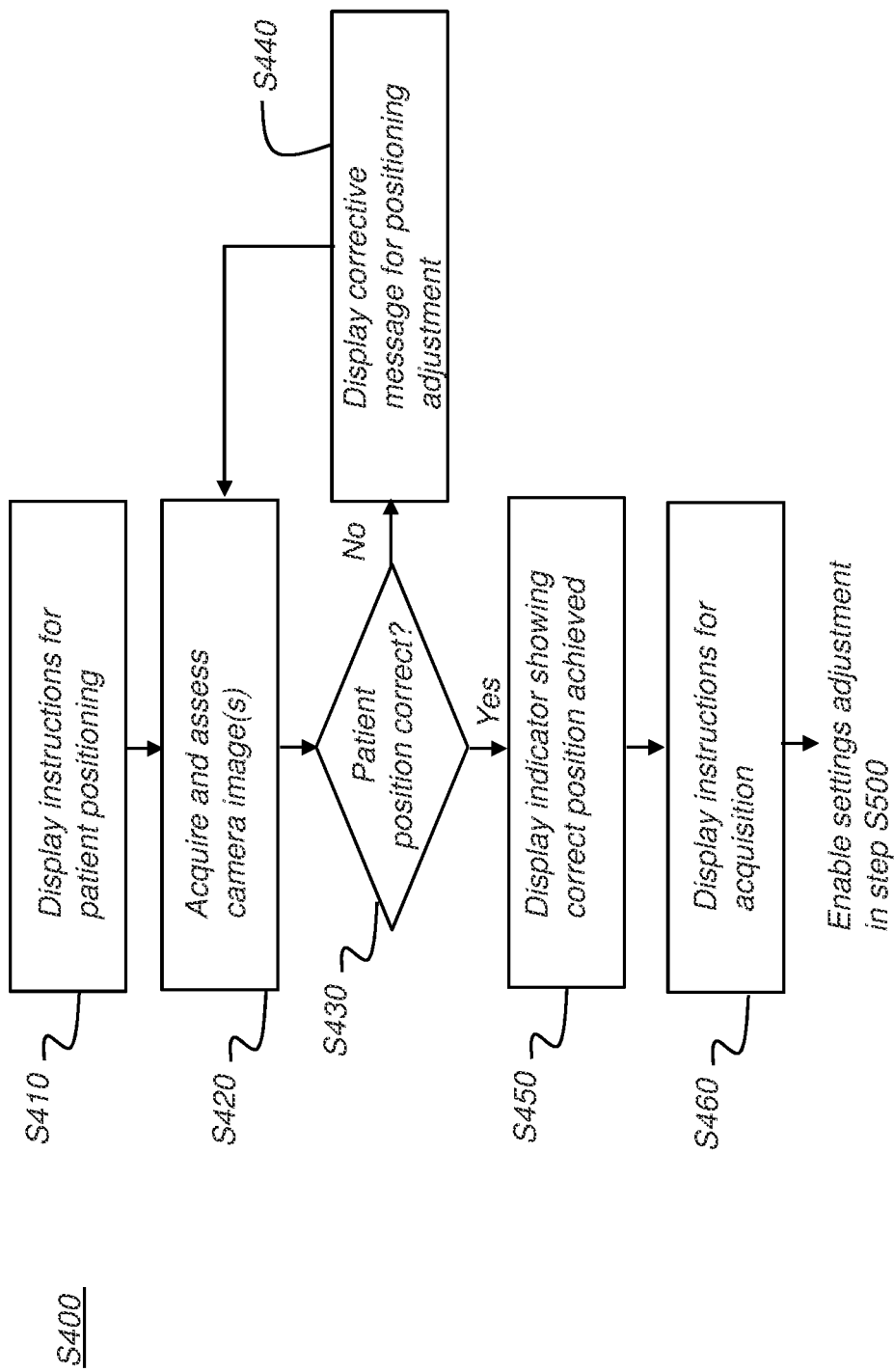
FIG. 5 is a logic flow diagram for an exemplary patient positioning sequence.

The logic flow diagram of FIG. 5 describes exemplary system behavior to support portions of patient positioning step S400 of FIG. 3 according to an embodiment of the present disclosure. With fiducial markings in position for patient guidance, an instructions presentation step S410 uses one or more of display 28, audio instructions over speaker 14, projected light patterns, or display indicators to instruct the patient on anatomy positioning needed for the specified exam.

According to an embodiment of the present disclosure, animation is used to teach the patient how to take a suitable position against the DR detector. A motion picture presentation, accompanied by audio, depicts a model patient moving toward the detector and taking up the appropriate position for the specified image.

A camera image acquisition step S420, which can execute throughout patient positioning and image acquisition processing, can repeatedly capture image content of the patient in order to determine patient position, posture, and anatomy placement, as well as distance from source and detector components, for example. A positioning decision step S430 can then determine whether or not the patient position with respect to the radiography system meets requirements for obtaining the specified radiographic image. If positioning adjustment is needed, a corrective message display step S440 can then present additional instructions for modifying anatomy placement. Instructions can be displayed on-screen or otherwise presented in audible or in graphic form.

Once patient positioning is suitable for the images to be obtained, an indicate correct position step S450 can execute, providing positive audible or visual feedback to the patient and to any staff in attendance. An instructions display step S460 can provide any further instruction to the patient, such as an admonition to breathe deeply, maintain a given position, or rest a limb or other body part on a supporting platform or other device.

Upon execution of instructions display step S460, patient positioning step S400 is complete and final configurations step S500 can be executed, as shown in the flow diagram of FIG. 3.

Employing Trained Logic

As noted in the description of processing in the FIG. 3 and FIG. 4 sequences, trained logic, equivalently termed machine learning in the context of the present embodiment and distinguished from conventional programming algorithms, can be used to support a number of processes for image acquisition and analysis. Machine learning techniques have been successfully adapted to tasks that relate to image classification and feature recognition. Particular steps of FIGS. 3, 4, and 5 wherein machine learning can be applied can include steps S400 and its substeps S410-S460, S500, S700, S720, S730, S740, and S750, among others.

According to an embodiment of the present disclosure, trained logic for supporting the basic processes of FIGS. 3-5 is available in the form of ML (machine learning) modules. Using a modular approach, each module is dedicated to a particular task according to factors such as type of image and stage in the acquisition process. For example, a particular ML module may execute for QC analysis in step S700 when the type of image obtained is a chest x-ray and the patient is positioned for a PA (posteroanterior) view. A different ML module may execute for an x-ray of the left shoulder. Separating QC analysis tasks according to anatomy imaged can help to simplify training of ML logic and allows for alternative image processing software algorithms to be used where full ML capabilities are not needed or where suitable ML modules are still in development.

The machine learning models used can employ any of a number of appropriate machine learning types. Machine learning, as used herein can include supervised learning, in which labeled input and output examples are provided and system logic executes continuously in order to adjust internal variables and cost functions that direct decision making in the internal logic. Supervised learning can use any of a number of known techniques including regression logic, back propagation neural networks, random forests, decision trees, and other methodologies. Alternately, unsupervised learning methods can be adopted, such as using K-means clustering or a priori algorithms, for example.

Machine learning or trained logic can alternately employ various training approaches such as semi-supervised learning or other suitable learning method. Reinforcement learning methods can be used, such as methods that use a Q-learning algorithm or use temporal difference learning, or other appropriate learning style. Each portion of the machine learning application can implement any one or more of: a regression algorithm (e.g., ordinary least squares, logistic regression, stepwise regression, multivariate adaptive regression splines, locally estimated scatterplot smoothing, etc.), an instance-based method (e.g., k-nearest neighbor, learning vector quantization, self-organizing map, etc.), a regularization method (e.g., ridge regression, least absolute shrinkage and selection operator, elastic net, etc.), a decision tree learning method (e.g., classification and regression tree, iterative dichotomiser, chi-squared automatic interaction detection, decision stump, random forest, multivariate adaptive regression splines, or gradient boosting machine, for example), a Bayesian method (e.g., naïve Bayes, averaged one-dependence estimators, or Bayesian belief network), a kernel method (e.g., a support vector machine, a radial basis function, a linear discriminate analysis, etc.), a clustering method (e.g., k-means clustering, expectation maximization, etc.), an associated rule learning algorithm (e.g., an a priori algorithm, an Eclat algorithm, etc.), an artificial neural network model (e.g., a Perceptron method, a back-propagation method, a Hopfield network method, a self-organizing map method, a learning vector quantization method, etc.), a deep learning algorithm (e.g., a restricted Boltzmann machine, a deep belief network method, a convolution network method, a stacked auto-encoder method, etc.), a dimensionality reduction method (e.g., principal component analysis, partial lest squares regression, Sammon mapping, multidimensional scaling, projection pursuit, etc.), an ensemble method (e.g., boosting, boostrapped aggregation, AdaBoost, stacked generalization, gradient boosting machine method, random forest method, etc.), and any suitable form of machine learning algorithm.

Each processing portion of the system can additionally or alternatively follow a probabilistic module, heuristic module, deterministic module, or any other suitable module leveraging any other suitable computation method, machine learning method or combination thereof. Any suitable machine learning approach can be incorporated into the system as a machine learning module, as appropriate.

In order to execute various steps in the process flow shown in FIGS. 3 and 4, a machine learning processor can be trained to evaluate image quality and image content and features using deep learning methods. Deep learning (e.g., deep structured learning, hierarchical learning, or deep machine learning) models high-level abstractions in data. In deep learning, the input features required to train machine logic are not explicitly defined or engineered by the user, as is the case using more "shallow" learning algorithms. The machine learning output can be highly abstract (for example, judgement on image quality, assessment of the condition for the imaged patient anatomy) relative to the input (a lengthy vector that lists pixel values).

Deep learning is a subset of machine learning that uses a set of algorithms to model high-level abstractions in data using a deep graph with multiple processing layers including linear and non-linear transformations. While many machine learning systems are seeded with initial features and/or network weights to be modified through learning and updating of the machine learning network, a deep learning network trains itself to identify "good" features for analysis. Using a multilayered architecture, machines employing deep learning techniques can often process raw data better than machines using conventional machine learning techniques, particularly where judgment and analysis/assessment normally reserved for the skilled practitioner/observer have normally been needed. Examining data for groups of highly correlated values or distinctive themes is facilitated using different layers of evaluation or abstraction. Deep learning in a neural network environment includes numerous interconnected nodes referred to as neurons. Input neurons, activated from an outside source, activate other neurons based on connections to those other neurons which are governed by the machine parameters. A neural network behaves in a certain manner based on its own parameters. Learning refines the machine parameters, and, by extension, the connections between neurons in the network, such that the neural network behaves in a desired manner.

A neural network provides deep learning by using multiple processing layers with structures adapted to provide multiple non-linear transformations, where the input data features are not engineered explicitly. In embodiments of the present disclosure, a deep neural network can process the input image data content by using multiple layers of feature extraction to identify features of the image content, such as for image quality measurement or for assessing patient condition. The machine training itself is typically run in unsupervised mode, learning the features to use and how to classify given an input sample (i.e., feature vector), Other deep learning, sparse auto-encoding models may alternately be trained and applied for one or more processes in the FIG. 3 or FIG. 4 sequence.

By applying a modular approach for design of control software, an embodiment of the present disclosure can allow a combination of programmed logic and trained logic based on machine learning to be used in overall image acquisition and processing. For example, the complete process described herein can be orchestrated using trained logic that invokes either a programmed logic module or a trained logic module for any particular task.

The invention has been described in detail, and may have been described with particular reference to a suitable or presently preferred embodiment, but it will be understood that variations and modifications can be effected within the spirit and scope of the invention. The presently disclosed embodiments are therefore considered in all respects to be illustrative and not restrictive. The scope of the invention is indicated by the appended claims, and all changes that come within the meaning and range of equivalents thereof are intended to be embraced therein.

The invention claimed is:

1. A computer system implemented method for radiographic imaging comprising:
    identifying a subject anatomy for radiographic imaging;
    automatically identifying a position of a subject with respect to an X-ray imaging apparatus from one or more sensor signals and, if necessary, outputting a guidance signal to communicate repositioning instructions to the subject;
    generating configuration signals for configuring and positioning components of the imaging apparatus, wherein the imaging apparatus components comprise at least an x-ray source and a DR detector for the radiographic imaging;
    generating one or more technique signals to set imaging exposure levels according to the identified subject anatomy;
    acquiring a radiographic image of the subject anatomy by automatically energizing the x-ray source;
    analyzing the acquired radiographic image of the subject anatomy using trained logic to determine clinical diagnostic suitability of the acquired radiographic image; and
    assessing the acquired radiographic image of the subject anatomy according to trained logic to identify one or more abnormalities in the subject anatomy.

2. The method of claim 1, further comprising recording the assessment of the subject anatomy and displaying the assessment on a display.

3. The method of claim 1, further comprising identifying the subject anatomy by receiving anatomy data entered by the subject.

4. The method of claim 1, further comprising identifying the subject anatomy by receiving anatomy data transmitted electronically over a network.

5. The method of claim 1, further comprising automatically identifying a position of a subject by analyzing a camera image of the subject.

6. The method of claim 1, further comprising automatically identifying the position of the subject relative to one or more fiducial markers pre-positioned at the x-ray imaging apparatus.

7. The method of claim 1, wherein outputting a guidance signal to communicate repositioning instructions to the subject comprises displaying an animation for the subject.

8. The method of claim 1, further comprising determining an exposure period of the x-ray source according to the identified subject anatomy.

9. The method of claim 1, wherein the step of assessing comprises identifying a fracture in a bone of the subject.

* * * * *